Figure 1:
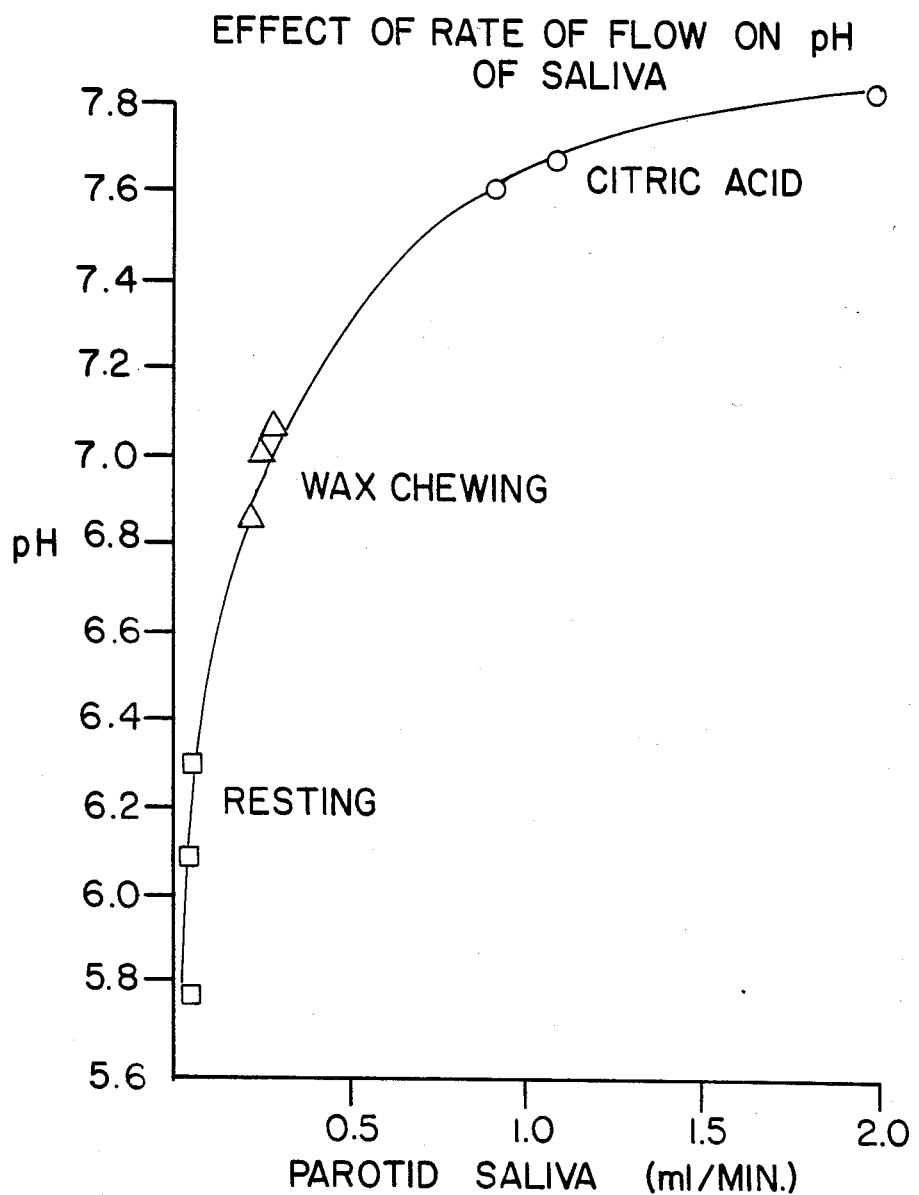

United States Patent [19]

Hoerman et al.

[11] Patent Number: 4,568,537

[45] Date of Patent: Feb. 4, 1986

[54] DENTAL HEALTH METHOD EMPLOYING CHEWING GUM

[75] Inventors: Kirk C. Hoerman, Lake Forest; Charles S. Nevin, Wilmette, both of Ill.

[73] Assignee: Wm. Wrigley Jr. Company, Chicago, Ill.

[21] Appl. No.: 501,532

[22] Filed: Jun. 6, 1983

[51] Int. Cl.³ .............................................. A61K 9/68
[52] U.S. Cl. ................................. 424/48; 426/3; 426/5
[58] Field of Search .................... 424/48; 426/3, 5

[56] References Cited

U.S. PATENT DOCUMENTS

| | | | |
|---|---|---|---|
| 1,630,763 | 5/1927 | Raymer et al. | 424/48 |
| 2,812,256 | 11/1957 | Nerfin | 99/135 |
| 3,632,358 | 1/1972 | Echeandra et al. | 99/135 |
| 4,064,274 | 12/1977 | Mackay et al. | 426/3 |
| 4,065,578 | 12/1977 | Reggio et al. | 426/3 |
| 4,085,227 | 4/1978 | Mackay et al. | 426/3 |
| 4,088,788 | 5/1978 | Ream et al. | 426/3 |
| 4,134,999 | 1/1979 | Muhler et al. | 426/3 |
| 4,151,270 | 4/1979 | Ream et al. | 424/48 |
| 4,208,431 | 6/1980 | Friello et al. | 426/3 |
| 4,217,368 | 8/1980 | Witzel et al. | 426/3 |
| 4,248,895 | 2/1981 | Stroz et al. | 426/3 |
| 4,250,196 | 2/1981 | Friello et al. | 426/5 |
| 4,252,830 | 2/1981 | Kehoe et al. | 426/3 |
| 4,271,197 | 6/1981 | Hopkins et al. | 426/3 |
| 4,271,199 | 6/1981 | Cherukuri et al. | 426/5 |
| 4,301,178 | 11/1981 | Witzel et al. | 426/5 |
| 4,316,915 | 2/1982 | Friello et al. | 426/5 |
| 4,317,837 | 3/1982 | Kehoe et al. | 426/3 |
| 4,328,249 | 5/1982 | Mackay et al. | 426/3 |
| 4,352,825 | 10/1982 | Cherukuri et al. | 426/5 |
| 4,352,853 | 10/1982 | Cherukuri et al. | 426/5 |
| 4,357,354 | 11/1982 | Kehoe et al. | 426/3 |
| 4,399,154 | 8/1983 | Puglia | 426/5 |
| 4,400,372 | 8/1983 | Muhler et al. | 424/48 |

OTHER PUBLICATIONS

Kleber, J. et al., "Changes in Salivary pH After Ingestion of Sorbitol Tablets Containing Various Food Acidulatns", *J Dent Res*, vol. 58 (6) pp. 1564–1565 (Jun. 1979).

G. N. Jenkins, "Salivary Effects on Plaque pH" (In *Saliva and Dental Caries*, Eds. Kleinberg, I., Ellison, S., and Mandel, I., Sp. Supp. *Microbiology Abstracts*, p. 307 (1979)).

*Primary Examiner*—Shep K. Rose
*Attorney, Agent, or Firm*—William, Brinks, Olds, Hofer, Gilson & Lione Ltd.

[57] ABSTRACT

A method for promoting dental health in which chewing gum is employed to alter the oral environment to provide natural resistance to dental caries. The method involves chewing a sugarless gum which contains a relatively insoluble, hydrophobic food-grade organic acid, preferably adipic acid. Chewing of the gum gradually releases the acid from the gum at a desirably linear rate over a period of approximately 20 to 30 minutes. Release of the acid from the gum into the mouth stimulates an increase in salivary flow rate greater than that experienced during chewing a non-acidulated chewing gum, resulting in increases in salivary electrolytes and basic proteins and in the concentration of natural salivary bicarbonate to a level in excess of that necessary to neutralize the acidulant being released from the gum. The excess of natural salivary bicarbonate raises the salivary pH and plaque pH and neutralizes microbially-formed lactic acid responsible for tooth demineralization and resultant dental caries.

14 Claims, 6 Drawing Figures

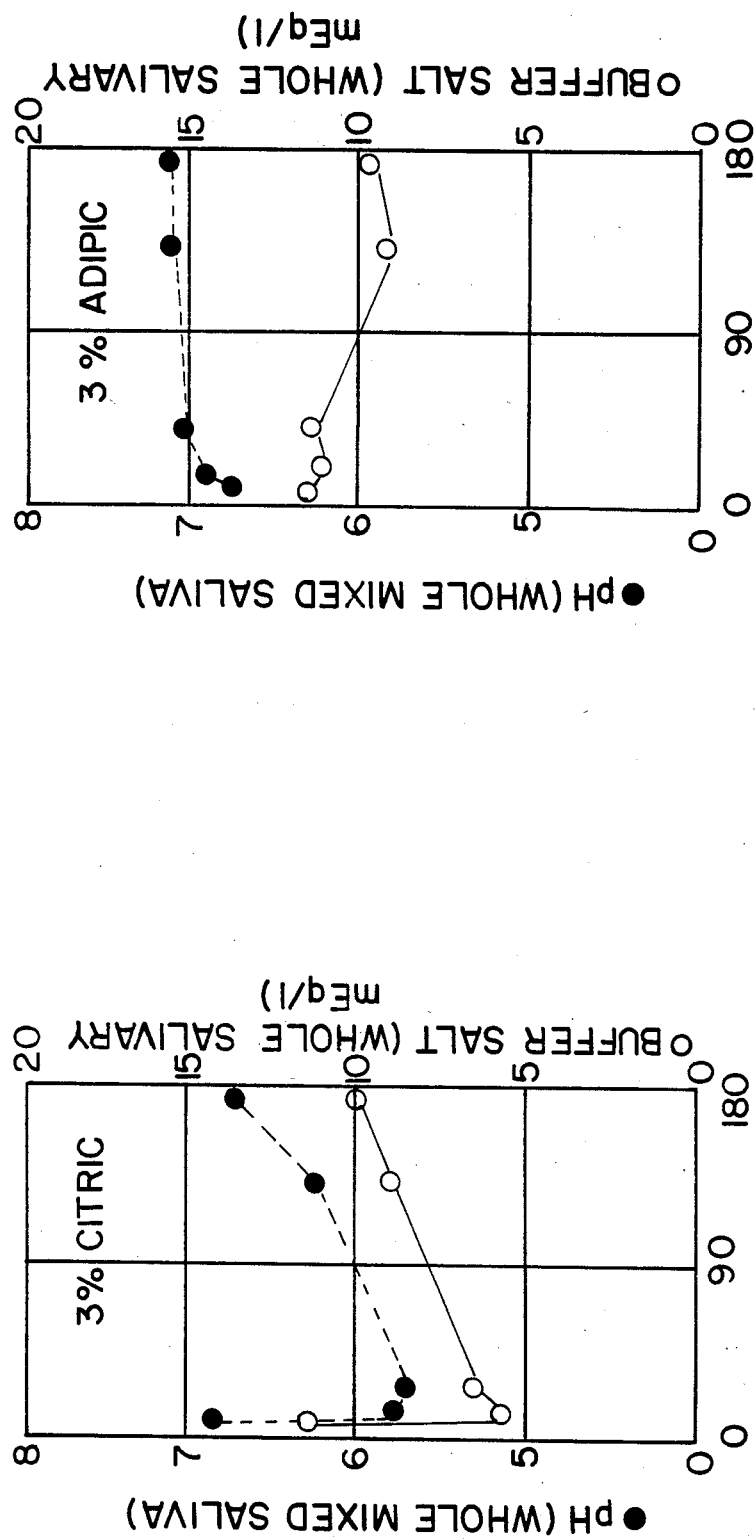

DENTAL HEALTH METHOD EMPLOYING CHEWING GUM

BACKGROUND OF THE INVENTION

This invention relates in general to a method for promoting dental health by preventing tooth demineralization and providing tooth remineralization and thereby reducing dental caries. The method employs a chewing gum containing a sparingly soluble food-grade acid.

Efforts have been made over the years to address the problem of dissolution or demineralization of tooth enamel and the resultant formation of dental caries. As is well known, dental plaque accumulates on the teeth as the result of the growth and metabolism of certain bacteria, such as *Streptococcus mutans*, which are nourished by cariogenic comestibles, particularly those containing sugars. Such bacteria are involved in the formation of dental plaque which accumulates as a deposit on the surfaces of teeth. The metabolism of bacteria within the plaque results in the generation of high levels of acids which are detrimental to the teeth and contribute to the production of dental caries. Chewing gums which have been developed in the past to inhibit the production of dental plaque have required therapeutic or anticariogenic agents which sometimes have undesirable side effects, require governmental approval, or both.

SUMMARY OF THE INVENTION

The present invention is directed to a method for preventing tooth demineralization and providing tooth remineralization by altering the oral environment to provide natural resistance to dental caries. The method involves chewing a sugarless gum which contains a relatively insoluble, hydrophobic food-grade acid, preferably adipic acid. Chewing of the gum effects gradual release of the acid from the gum at a desirably linear rate over a period of about 20 to 30 minutes during which the acid is effective to stimulate saliva at a flow rate greater than that experienced during chewing a non-acidulated chewing gum, with resultant proportional increases in salivary electrolytes and basic proteins and in the concentration of salivary bicarbonate whereby the salivary pH is elevated above that of unstimulated saliva. Most importantly, gradual release of the hydrophobic acidulant from the gum stimulates a natural secretion of salivary bicarbonate to a level in the mouth in excess of that necessary to neutralize the acidulant. The excess buffer thus generated raises the pH of the saliva and in turn the pH of dental plaque and thus effects a neutralization of harmful, microbially-formed lactic acid which initiates tooth demineralization and resultant dental caries. The chewing of the gum is further effective to achieve mechanical dental cleansing.

Thus, the present invention utilizes acids, heretofore generally considered to be detrimental to teeth, in a safe, natural system for promoting dental health in an enjoyable manner and at a low cost.

IN THE DRAWINGS

Figure 4:
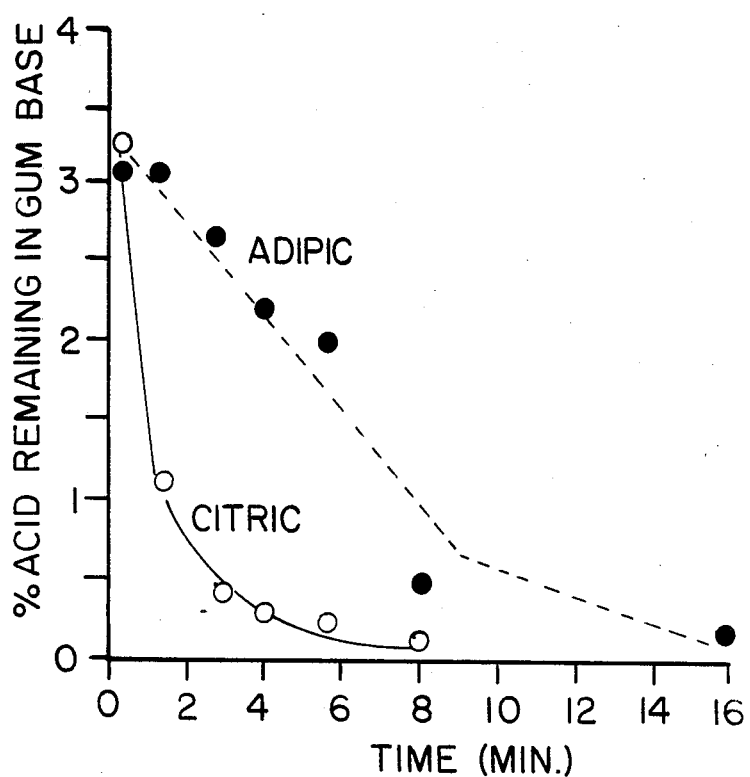
Figure 5:
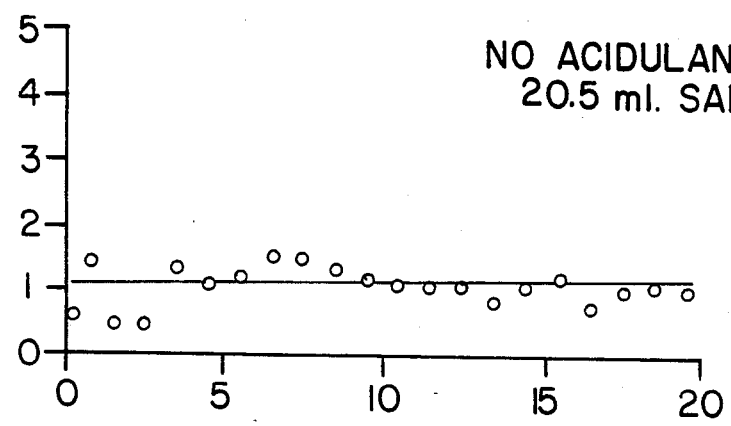
Figure 6:
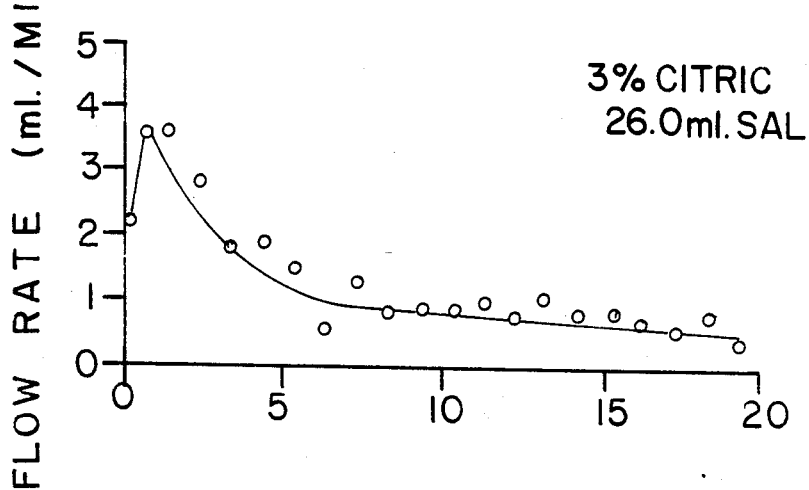
Figure 7:
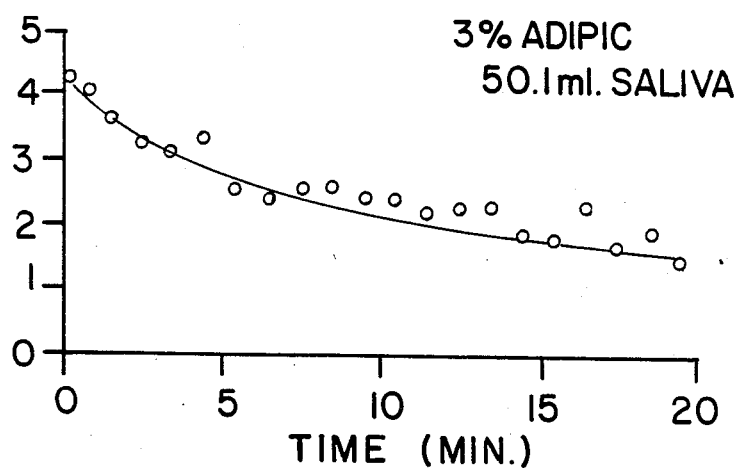

FIG. 1 is a graph of salivary pH as a function of parotid salivary flow rate (ml/min), FIG. 2 is a graph illustrating the comparative salivary pH - lowering effect of citric acid and adipic acid in chewing gum expressed in terms of salivary pH as a function of chewing time, FIG. 3 is a graph illustrating comparative release characteristics of adipic and citric acids from gum base expressed as percent of acid remaining in the gum base (after chewing for 0 to 16 minutes, FIG. 4 is a graph of salivary flow rate as a function of time with gum containing no acidulant, FIG. 5 is a graph of salivary slow rate as a function of time when gum containing 3% citric acid is chewed for 20 minutes, and FIG. 6 is a graph of salivary slow rate as a function of time when gum containing 3% adipic acid is chewed for 20 minutes.

DESCRIPTION OF THE INVENTION

The present invention utilizes salivary flow to promote dental health and to control tooth decay or dental caries. As is well known, salivation is an important physiological function which has several benefits in addition to those relating to digestion.

One of those benefits is the washing of tooth enamel surfaces and their surrounding soft tissues or gums. This washing provides a preventive effect against disease in direct relation to the rate of salivary flow from the four major salivary glands which empty into the human mouth under various stimulations.

Other beneficial effects of salivation arise from the action of the 1.0% dissolved constituents which exist in saliva, which is typically 99.0% water. Proteins make up about 0.3% of such dissolved constituents and function to degrade starches and other substances in the mouth by way of enzymic actions in preparation for digestion. More importantly for present purposes, such proteins assist in the neutralization of acids produced in the mouth or introduced through foods and beverages. For example, sialin is a protein-like molecule in saliva which is believed to reduce acid levels in the mouth by acting on acid-producing bacteria and is therefore thought to be anticariogenic.

Inorganic constituents such as calcium, phosphorus, bicarbonate and other electrolytes occur in saliva and make up the remaining 0.7% of the solid constituents. Calcium and phosphorus are present at levels which saturate the saliva solution in order to prevent dissolution of tooth enamel under normal circumstances and effect remineralization of early decay enamel surfaces.

Resting or unstimulated salivary flow is typically less than 0.1 ml/minute. Non-resting or stimulated salivary flow can occur due to aromas, flavors, tastes (either sweet, sour, salty or bitter) and masticatory actions. Chewing alone can increase the flow rate by as much as 400%. Sour foods are far more effective in increasing flow rate and volume, often as much as 2,000% of resting flow.

Saliva from stimulated glands differs qualitatively from that derived from resting glands, the most dramatic difference being in the pH, which varies from the acidic pH level of 5.5 to the more basic pH level of 7.8 during maximum saliva flow due to the higher level of bicarbonate ion then present in the fluid. The concentration of calcium, phosphorus and other electrolytes also rises when the saliva flow is at an increased rate. After maximum flow is established, the concentration of salivary electrolytes continues to rise and may not achieve a steady state even after 15 minutes of stimulated flow.

The method of the present invention utilizes the fact that the concentration of bicarbonate in saliva (as indicated by saliva pH) increases as the rate of flow of the saliva from the salivary glands increases, as illustrated in the graph of FIG. 1.

Because the bicarbonate acts as a buffer or acid-neutralizing agent, in the present invention it raises the pH of both the saliva and the plaque deposited on tooth enamel where high levels of acid are produced by the metabolism of bacteria. The excess bicarbonate serves as a natural buffering agent which neutralizes microbially-formed lactic acid responsible for the initiation of tooth demineralization and resultant dental caries.

Chewing gum not only provides the flavor and chewing factors for saliva stimulation but also achieves mechanicl dental cleansing, making it an ideal and natural mechanism for promoting dental health.

Although relatively soluble food acids (such as citric, tartaric and malic acids, for example) are sometimes added to chewing gum usually at a level of 1% or less to impart tartness, such acids dissipate rapidly from the chewing gum and occur in such immediate and high concentrations in the saliva that the natural acid-neutralizing action of bicarbonate is overcome, resulting in a sudden lowering of the pH which has a deleterious effect on teeth because of the resultant dissolution of minerals in tooth enamel. The graph FIG. 2 illustrates the pH-lowering effect of 3% citric acid in chewing gum as compared with 3% adipic acid.

The present invention achieves the desirable effect of a prolonged stimulation of saliva and acid buffering over an extended time period, on the order of 20 to 30 minutes, through a slow release of a sparingly soluble food acidulant from chewing gum base during chewing of the gum. Such a release characteristic produces an overwhelming quantity of bicarbonate buffer which raises the pH of both the saliva and the plaque. Unlike soluble acidulants, relatively insoluble hydrophobic acids having a water solubility of less than about 20% by weight at 37° C., preferably adipic, fumaric, succinic, suberic, sebacic, azelaic and pimelic acids, are persistent in the gum base during chewing and do not produce a drastic drop in the pH of saliva. For this reason, higher acid levels can be used without producing excessive and unpleasant tartness. The chewing of the dental health gum brings about a slow, linear release of the acid from the gum base such that a slowly decreasing concentration of acid in the gum base occurs as opposed to the rapidly declining exponential release of soluble or hydrophilic food acidulants. Further, as would be expected from the nearly linear release of adipic acid from the dental health gum, it has been found that the gum, throughout the 20–30 minute period of acid release, promotes a more nearly constant stimulation of parotid salivary flow as compared with gums containing rapidly dissipated acidulants such as citric acid which cause an initial stimulation of the saliva flow rate followed by an abrupt exponential decrease in rate. The of FIGS. 3–6 provide a comparison of the release characteristics of citric and adipic acid and further point out the differing effects these acids have not only upon the parotid salivary flow rate during chewing of acid-impregnated gum but also upon the total volume of saliva secreted when gums containing either acid are chewed for twenty minutes. As can be seen below, the 3% adipic acid gum stimulates nearly twice as much saliva as the citric acid gum.

It should further be noted that, in the graphs of FIGS. 3–6 which plot parotid salivary flow (ml/min) versus time (min), the initial deviation of the adipic acid graph from an expected and desired straight line function having a constant salivary flow-rate value is probably due to other ingredients in the gum which cause an initial increase in salivation by which are rapidly dissipated.

The use of chewing gum in the present invention which effects a slow, controlled release of acid from the gum is to be contrasted with the use of other delivery methods such as hard candy or chewing gum containing a rapidly released acid such as citric, malic, or tartaric acid. In the case of hard candy, high concentrations of acid overpowering the natural buffer capacity in saliva are delivered at a steady rate for a short period of time in combination with a high sugar content. Similarly, gum containing a rapidly-released acidulant also produces an abrupt drop in pH of the oral environment sometimes in combination with high sugar levels. Thus, the use of hard candy or chewing gums containing rapidly-dissipated acidulants, as contrasted with the present invention, enchances rather than suppresses cariogenicity in the oral environment.

During the 20 to 30 minutes acid release period in the present invention, the sustained acid and resulting taste stimulus is effective to invrease saliva to a flow rate greater than that experienced during chewing a nonacidulated chewing gum. The result is a proportional increase in dental washing, a proportional increase in the concentration of salivary electrolytes and basic proteins and, most importantly, a proportional increase in the concentration of natural salivary bicarbonate which, upon neutralizing the gum acidulant, results further in an elevation of the salivary pH above that of unstimulated saliva as well as an elevation of the plaque pH.

The dental health gum for use in the method of the present invention comprises gum base, a sugarless sweetener, flavoring and the relatively insoluble food-grade organic acid in an amount ranging from about 1.0 to about 6.0% by weight of the chewing gum composition.

The preferred food-grade acid is adipic acid in an optimum amount of about 2.0% by weight of the chewing gum composition. A second preference is fumaric acid in an optimum amount of about 4.0% by weight.

The sugarless sweetener in the chewing gum composition of the present invention can be a water-soluble bulking agent present in an amount ranging from about 30% to about 65% by weight of the entire chewing gum composition and may comprise a sugar alcohol or mixtures thereof selected from the group consisting of sorbitol, mannitol or xylitol. The sugarless sweetener may be an artificial high-potency sweetener, that is, one having a sweetness greater than 20 times that of sucrose such as saccharin, thaumatin, a cyclamate or acesulfame K. However, one preferred such sweetener is the dipeptide sweetener aspartame (L-aspartyl-L-phenylalanine methyl ester, originally disclosed in U.S. Pat. Nos. 3,492,131 and 3,642,491) which is used in an amount of about .025% to about 2.0% but preferably about 0.1% by weight of the chewing gum composition. The bulking agent may comprise a partially indigestible and noncariogenic carbohydrate such as polydextrose.

EXAMPLE I

A dental health gum suitable for use in the method of the present invention can be made according to the following formulation:

| Ingredient | Percent By Weight |
| --- | --- |
| Gum Base | 26.91 |
| Glycerine | 0.80 |
| Sorbitol | 39.41 |
| 70% Sorbitol Solution | 17.31 |
| Mannitol | 12.01 |
| Lemon Flavor | 1.56 |
| Adipic Acid | 2.00 |

This gum exhibits a mild, pleasant and long-lasting tartness which compliments the lemon flavor.

EXAMPLE II

An aspartame dental health gum preferred for use in the present invention can be manufactured according to the following formulation:

| Ingredient | Percent By Weight |
| --- | --- |
| Gum Base | 26.91 |
| Glycerine | 0.80 |
| Sorbitol | 38.31 |
| 70% Sorbitol Solution | 17.31 |
| Mannitol | 12.01 |
| Lemon Flavor | 1.56 |
| Aspartame | 0.10 |
| Adipic Acid | 3.00 |

The aspartame provides improved sweetness for the chewing gum and the adipic acid contributes to the stabilization of the aspartame.

EXAMPLE III

Another gum suitable for use in the present invention can include fumaric acid in the following formulation:

| Ingredient | Percent By Weight |
| --- | --- |
| Gum Base | 26.91 |
| Glycerine | 0.80 |
| Sorbitol | 37.97 |
| 70% Sorbitol Solution | 17.31 |
| Mannitol | 12.01 |
| Apple Flavor | 1.00 |
| Fumaric Acid | 4.00 |

For maximum dental health benefit, the chewing gum should be chewed after meals or snacks to raise, for an extended period of time, the plaque pH which is depressed by bacteria acting upon residual food material. Chewing of the gum increases salivary washing and provides mechanical removal of food debris.

The embodiments of the invention in which an exclusive property or privilege is claimed are defined as follows:

1. A method of preventing tooth dimineralization and providing tooth remineralization comprising the step of chewing regularly after meals and snacks and for a period of at least 20 minutes, a sugarless gum containing a food grade organic acid in an amount ranging from about 1.0% to about 6.0% by weight of the chewing gum composition, the acid having a water solubility of less than about 20.0% by weight at 37° C. or a degree of hydrophobicity sufficient for retention of the acid in a nonpolar chewing gum base yet releasable therefrom over an extended period of time during chewing of the gum, the acid being released during chewing of the gum to stimulate saliva at a flow rate greater than that experienced during chewing a non-acidulated chewing gum in order to achieve a proportional increase in the concentration of salivary electrolytes and basic proteins and a proportional increase in the concentration of salivary bicarbonate which neutralizes the acid and raises the salivary pH above that of unstimulated saliva.

2. The method of claim 1 wherein the organic acid is selected from the group consisting of adipic, fumaric, suberic, sebacic, azelaic and pimelic acids.

3. The method of claim 1 wherein the organic acid is adipic acid.

4. The method of claim 3 wherein the adipic acid is present in an amount ranging from abut 2.0% to 3.5% by weight of the chewing gum composition.

5. The method of claim 1 wherein the organic acid is fumaric acid.

6. The method of claim 5 wherein the fumaric acid is present in an amount of about 4.0% by weight of the chewing gum composition.

7. The method of claim 1 wherein the organic acid has a water solubility of less than about 7.0% by weight at 37° C.

8. The method of claim 1 wherein the organic acid is released from the gum at a non-exponential rate over a time period of about 20 to 30 minutes.

9. The method of claim 1 wherein the sweetening ingredient of the sugarless gum composition is a sugar alcohol or a combination of sugar alcohols.

10. The method of claim 9 wherein the sugar alcohol or combination of sugar alcohols is selected from the group consisting of sorbitol, mannitol and xylitol.

11. The method of claim 1 wherein the sweetening ingredient of the sugarless gum composition is a sugarless high-intensity sweetener.

12. The method of claim 11 wherein the sugarless high-intensity sweetener is selected from the group consisting of aspartame, saccharin, thaumatin, a cyclamate or acesulfame K.

13. The method of claim 1 wherein chewing of the gum is further effective to achieve mechanical dental cleansing.

14. An anti-cariogenic, tooth decay preventive dental health method comprising the step of chewing a sugarless chewing gum composition containing food-grade organic acid in an amount ranging from about 1.0% to about 6.0% by weight of the chewing gum composition, the acid having a water solubility of less than 20.0% by weight at 37° C. or a degree of hydrophobicity sufficient for retention of the acid in a non-polar chewing gum base yet releasable therefrom over an extended period of time of about 20 to 30 minutes during chewing of the gum, the acid being released during chewing of the gum to stimulate salivary flow at a rate greater than that occurring during chewing a non-acidulated gum, resulting in a proportional increase in glandular secretion of salivary electrolytes and basic proteins and a proportional increase in the concentration of natural salivary bicarbonate in excess of that necessary to neutralize the acid released from the chewing gum, said excess bicarbonate then serving as a natural buffering agent to elevate salivary and plaque pH and neutralize microbially-formed lactic acid which initiates tooth demineralization and resultant dental caries, whereby such increases in salivary constituents provide host resistance to cariogenic challenge.

* * * * *